United States Patent
Barbosa

(10) Patent No.: US 10,710,885 B2
(45) Date of Patent: Jul. 14, 2020

(54) GERMANIUM-68 SOURCE MATERIAL AND CALIBRATION DEVICES THAT INCLUDE SUCH SOURCE MATERIAL

(71) Applicant: Curium US LLC, St. Louis, MO (US)

(72) Inventor: Luis Antonio M. M. Barbosa, Bergen (NL)

(73) Assignee: CURIUM US LLC, St. Louis, MO (US)

(*) Notice: Subject to any disclaimer, the term of this patent is extended or adjusted under 35 U.S.C. 154(b) by 0 days.

(21) Appl. No.: 16/325,891

(22) PCT Filed: Aug. 14, 2017

(86) PCT No.: PCT/US2017/046696
§ 371 (c)(1),
(2) Date: Feb. 15, 2019

(87) PCT Pub. No.: WO2018/035009
PCT Pub. Date: Feb. 22, 2018

(65) Prior Publication Data
US 2019/0218105 A1    Jul. 18, 2019

Related U.S. Application Data

(60) Provisional application No. 62/375,641, filed on Aug. 16, 2016.

(51) Int. Cl.
| | | |
|---|---|---|
| *C01B 37/02* | (2006.01) | |
| *G01T 1/29* | (2006.01) | |
| *G01T 7/00* | (2006.01) | |
| *C01G 17/02* | (2006.01) | |
| *G01T 1/169* | (2006.01) | |
| *A61B 6/00* | (2006.01) | |

(Continued)

(52) U.S. Cl.
CPC .............. *C01B 37/02* (2013.01); *A61B 6/037* (2013.01); *A61B 6/4258* (2013.01); *A61B 6/585* (2013.01);
(Continued)

(58) Field of Classification Search
CPC ....... C01B 37/02; A61B 6/037; A61B 6/4258; A61B 6/585; B01J 29/047; C01G 17/006;
(Continued)

(56) References Cited

U.S. PATENT DOCUMENTS 5,512,267 A  *  4/1996  Davis ..................... C01B 39/12
                                                        208/46
7,825,372 B2 * 11/2010  Allberg .................... G01T 1/20
                                                        250/252.1
(Continued)

FOREIGN PATENT DOCUMENTS

| CN | 101593567 A | 12/2009 |
| CN | 203346055 U | 12/2013 |

OTHER PUBLICATIONS

Kosslick H et al: "Synthesis and 1-27 Characterization of Ge-ZSM-5 Zeolites", Journal of Physical Chemistry, American Chemical Society, US, vol. 97, No. 21, Jan. 1, 1993 (Jan. 1, 1993), pp. 5678-5684, XPQ02997494, ISSN: 0022-3654, DOI: 10.1021/J100123A036 p. 5678, right-hand col.—p. 5679, left-hand col.

(Continued)

*Primary Examiner* — Taeho Jo
(74) *Attorney, Agent, or Firm* — Armstrong Teasdale LLP

(57) ABSTRACT

Calibration devices including germanium-68 source material are disclosed. The source material may be a matrix material (e.g., zeolite) in which germanium-68 is isomorphously substituted for central atoms in tetrahedra within the matrix material. Methods for preparing such calibration devices are also disclosed.

20 Claims, 3 Drawing Sheets

(51) Int. Cl.
    *C01G 17/00*    (2006.01)
    *A61B 6/03*    (2006.01)
    *H01L 31/00*    (2006.01)
    *B01J 29/04*    (2006.01)

(52) U.S. Cl.
    CPC .......... *B01J 29/047* (2013.01); *C01G 17/006* (2013.01); *C01G 17/02* (2013.01); *G01T 1/169* (2013.01); *G01T 1/2985* (2013.01); *G01T 7/005* (2013.01); *H01L 31/00* (2013.01); *C01P 2002/30* (2013.01); *C01P 2002/77* (2013.01); *C01P 2004/30* (2013.01); *C01P 2006/88* (2013.01)

(58) Field of Classification Search
    CPC ....... C01G 17/02; G01T 1/169; G01T 1/2985; G01T 7/005; H01L 31/00; C01P 2002/30; C01P 2002/77; C01P 2004/30
    USPC ..................................................... 250/252.1
    See application file for complete search history.

(56) References Cited

U.S. PATENT DOCUMENTS

| | | | | |
|---|---|---|---|---|
| 2009/0194677 | A1* | 8/2009 | Allberg | G01T 1/20 250/252.1 |
| 2009/0283668 | A1* | 11/2009 | Gilbertson | A61B 6/037 250/252.1 |
| 2013/0075599 | A1* | 3/2013 | Allberg | G21G 4/08 250/252.1 |
| 2017/0266328 | A1* | 9/2017 | Wall | A61K 51/1251 |

OTHER PUBLICATIONS

C. T. G. Knight et al: "Silicon-29 NMR 1-27 structural characterization of two novel germanosilicate cages in a tetramethylammonium germanosilicate solution", Journal of the American Chemical Society, vol. 108, No. 1, Jan. 1, 1986 (Jan. 1, 1986), pp. 30-33, XP055420389, US ISSN: 0002-7863, DOI: 10.1021/ia00261a007 p. 31.

Frick R et al., "Synthesis and Characterization of Ge-ZSM-5 Zeolites", J. Phys. Chem. Published 1993, pp. 5678-5684, vol. 97.

O'Keefe et al., "Germanate Zeolites: Contrasting the Behavior of Germanate and Silicate Structures Built from Cubic T8O20 Units (T= Ge or Si)", Chem. Eur. J., Published 1999, pp. 2796-2801, vol. 5.

Davis M et al., "Zeolite and Molecular Sieve Synthesis", Chem. Mater. Published 1992, pp. 756-768, vol. 4.

Davis M et al., "Zeolite from a Materials Chemistry Perspective", Chem. Mater. Published 2013, pp. A-G.

Moses et al., "Timing and Calibration in PET Using a Time Alignment Probe", IEEE Transactions on Nuclear Science. Published 2005, pp. 1-6, vol. LBNL-59117.

Zimmerman et al., "Calibrations of Large-Volume, Solid Ge-68 Phantom Sources for Monitoring PET Scanner Performance in Clinical Trials", NIST Physical Measurement Laboratory. Published 2013, pp. 1.

"PET and PET-CT Ge-68 Reference and Calibration Sources", Epsilon Electronics. Published 2009, pp. 1-4.

Rimer et al., "Self-Assembly and Phase Behavior of Germanium Oxide Nanoparticles in Basic Aqueous Solutions", Langmui. Published 2007, pp. 2784-2791, vol. 23.

Davis et al., "Zeolites from a Materials Chemistry Perspective", Chemistry of Materials. Published 2013, pp. 239-245, vol. 26.

Cheng et al., "Preparation of 68Ge/68Ga generator with a binary Ga/Ag electrodepositions as solid target", Journal of Radioanalytical Chemistry. Published 2000, pp. 25-30, vol. 245.

Sen et al., "Choice of Inorganic Materials as 68Ge/68Ga Generator: An Intercomparison", Ion Exchange Letters. Published 2011, pp. 32-43, vol. 4.

"CT and PET/CT", GE HC. Published 2013, pp. 1-30.

PCT International Search Report and Written Opinion, Application No. PCT/US2017/046696, dated Nov. 23, 2017, 28 pps.

* cited by examiner

GERMANIUM-68 SOURCE MATERIAL AND CALIBRATION DEVICES THAT INCLUDE SUCH SOURCE MATERIAL

CROSS-REFERENCE TO RELATED APPLICATIONS

This application is a 35 U.S.C. § 371 national stage of International Application No. PCT/US2017/046696, filed Aug. 14, 2017, which claims the benefit of priority to U.S. Provisional Patent Application No. 62/375,641, filed Aug. 16, 2016, both of which are incorporated herein by reference in their entirety.

FIELD OF THE DISCLOSURE

The field of the disclosure relates to solid-state germanium-68 source material and calibration devices that include such source material to calibrate radiation detectors. The calibration source material may be crystalline and germanium-68 may be isomorphously substituted for other central atoms of the crystalline matrix material.

BACKGROUND

Positron emission tomography (PET) is an in vivo imaging method that uses positron emitting radiotracers to track the biochemical, molecular, and/or pathophysiological processes in humans and animals. In PET systems, positron-emitting isotopes serve as beacons for identifying the exact location of diseases and pathological processes under study without surgical exploration of the human body. With these non-invasive imaging methods, the diagnosis of diseases may be more comfortable for patients, as opposed to the more traditional and invasive approaches, such as exploratory surgeries.

During PET imaging, PET gamma ray detectors (i.e., cameras or scanners) detect pairs of gamma rays that are emitted by the radiotracers. The PET detectors are periodically calibrated to assure function and accuracy of the equipment. Calibration may involve imaging of a calibration device (sometimes referred to as a calibration source) that includes a source of radioactive material that emits a known amount of radiation. The PET camera or scanner images the device and the results are compared to the amount of radiation the device was expected to emit based on the amount of radioactive material in the calibration device and/or based on measured activity.

One group of calibration devices is based on decay of germanium-68 ("Ge-68"). Ge-68 has a half-life of about 271 days, decays by electron capture to Ga-68, and lacks any significant photon emissions. These properties make germanium-68 an ideal material for calibrating PET scanners and cameras. A plastic matrix is sometimes used to hold various calibration sources, however this approach sometimes suffers from leaching during use and is sometimes structurally weak. Resins used as a matrix may deteriorate and form gas inside the material.

There is a need for improved germanium-68 source materials for calibrating radiation scanners and cameras and for calibration devices that incorporate such materials.

This section is intended to introduce the reader to various aspects of art that may be related to various aspects of the disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

SUMMARY

One aspect of the present disclosure is directed to a solid-state germanium-68 source material. The germanium-68 source material includes a matrix material having a three-dimensional polyhedral crystal structure. The matrix material includes a first tetrahedra comprising a central atom, T, and oxygen, and has a formula $TO_4$. The central atom is selected from the group consisting of silicon, aluminum, zirconium and stable germanium. The matrix material includes a second tetrahedra. The second tetrahedra is a germanium-68 tetrahedra comprising germanium-68 and oxygen and has a formula $^{68}GeO_4$. The first tetrahedra and the germanium-68 tetrahedra are part of a three-dimensional polyhedral crystal structure.

Another aspect of the present disclosure is directed to a method for producing a germanium-68 source material. The source material includes a matrix material with germanium-68 isomorphously substituted therein. The method includes forming a crystallization starting mixture. The starting mixture has a source of a first central atom and a source of a second central atom. The first central atom is germanium-68 and the second central atom is selected from the group consisting of silicon, aluminum, zirconium and stable germanium. The starting mixture is heated to cause the material to crystallize and form germanium-68 tetrahedra and tetrahedra of the second central atom in a crystallized structure.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

DETAILED DESCRIPTION

Figure 1:
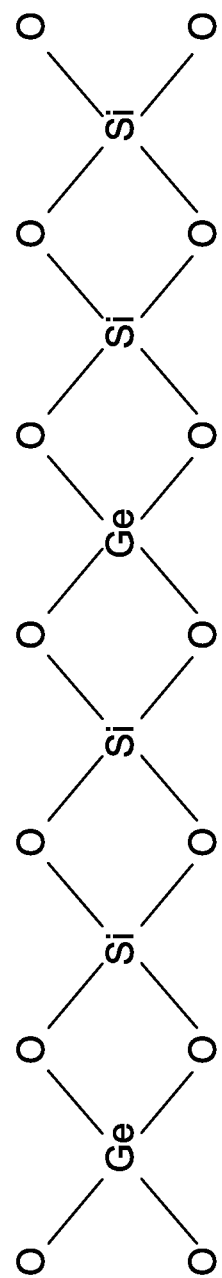
FIG. 1 is a schematic of a zeolite material in which germanium is isomorphously substituted for silicon central atoms.

Provisions of the present disclosure relate to germanium-68 source material for calibrating radiation detectors and for calibration devices used to calibrate such detectors. The source material may include a crystallized matrix material having germanium-68 incorporated therein. The germanium-68 is isomorphously substituted for one or more central atoms in the crystallized matrix material.

The germanium-68 material of embodiments of the present disclosure may be any material (which may be referred to herein as a "matrix material") which forms structures based on tetrahedral coordination. Generally the matrix material includes two different types of tetrahedra central atoms, one of which is germanium-68. Each tetrahedra atom has a central atom and a number (typically four) of coordination sites that are typically filled with oxygen. Each tetrahedral structure generally has a formula $TO_4$ wherein T is the central atom of the structure. The tetrahedra combine to form a polyhedral, three-dimensional crystal structure. Such three-dimensional structures may include various cavities or channels within the organized structure.

The central atoms, T, of the tetrahedral structures in the matrix material of embodiments of the present disclosure may be selected from silicon, aluminum, germanium and zirconium (e.g., $SiO_4$, $AlO_4$, $GeO_4$ and $ZrO_4$). In some embodiments, the matrix material comprises silicon tetrahedra ($SiO_4$) wherein germanium-68 is isomorphously substituted for silicon as the central atom of a number of tetrahedra within the matrix material. In this regard, it should be noted that the formula $TO_4$ as described herein represents the coordination of the tetrahedra (including shared oxygen) and that the material itself may have a different chemical formula. For example, the material itself may be silica ($SiO_2$), alumina ($AlO_2$), germania ($GeO_2$), zirconia ($ZrO_2$) and combinations of these materials with there being a tetrahedral coordination ($TO_4$) within the material.

The structure may be a zeolite material into which germanium-68 is isomorphously substituted for at least some silicon atoms within the zeolite material. Zeolite material generally includes two or more different types of tetrahedra that are linked to form the polyhedral, three-dimensional crystal structure of the zeolite material. As used herein, "zeolite" refers to any matrix of a first type of central atom (typically silicon), a second type of central atom and oxygen. The various central atoms that may be used include silicon, aluminum, germanium and zirconium. For example, the zeolite may be a matrix of silicon and aluminum (silico-aluminates) or a matrix of silicon and germanium (silicogermanates) or even zirconium and germanium (zirconogermanates).

The zeolite material may be a natural zeolite that is modified to include germanium-68 as an isomorphous substitute for the various central atoms of the tetrahedral structures within the material. More typically, the zeolite is a synthetic zeolite with germanium-68 atoms being incorporated isomorphously while producing the material. In some embodiments, the zeolite contains both silicon and aluminum tetrahedra (i.e., is a silico-aluminate) with germanium-68 being substituted for some of the silicon and/or aluminum atoms in the tetrahedral structures. In some embodiments, the zeolite is a pentasil-zeolite (such as ZSM-5) which contains isomorphous germanium-68. In some embodiments, the zeolite material contains stable germanium tetrahedra and aluminum tetrahedra with germanium-68 being substituted for some of the germanium atoms and/or aluminum atoms.

In such zeolite structures, the zeolite typically comprises three tetrahedral structures—silicon tetrahedra, germanium-68 tetrahedra and a third tetrahedra selected from the group consisting of aluminum, zirconium and stable germanium. In some embodiments, the third central atom is aluminum tetrahedra, the aluminum tetrahedra comprising aluminum and oxygen and having a structure $AlO_4$. In other embodiments, the third tetrahedra is stable germanium tetrahedra, the stable germanium tetrahedra comprising stable germanium and oxygen and having a formula $GeO_4$.

The amount of germanium-68 in the matrix material may be consistent with commercial calibration sources that include germanium-68. In some embodiments, formation of the crystallite material is controlled so as to form a source material with a particular activity range.

In addition to germanium-68, the zeolite matrix material may contain non-active (i.e., stable) germanium (e.g., germanium-74) that is isomorphously incorporated for some of the central atoms of the tetrahedral structures (FIG. 1). The molar ratio of non-active germanium to germanium-68 in the zeolite may be controlled to produce a calibration source with the desired activity.

Matrix materials which incorporate germanium-68 may be obtained by including germanium-68 in starting mixtures from which the matrix is crystallized. By including germanium-68, germanium-68 isomorphously substitutes for various of the tetrahedral central atoms of the structure (e.g., silicon, aluminum, zirconium or stable germanium). The crystallization starting mixture may include a source of germanium-68 as first central atoms and a source of second central atoms. The second central atoms may be selected from the group consisting of silicon, aluminum, zirconium and stable germanium.

In some particular embodiments, germanium-68 is substituted for stable germanium that is used to assemble the structure. Zeolite materials incorporating stable germanium may be prepared according to known methods such as, for example, as described in Kosslick et al., "Synthesis and Characterization of Ge-ZSM-5 Zeolites", J. Phys. Chem. 1993, 97(21), pp. 5678-5684, which is incorporated herein by reference for all relevant and consistent purposes.

In some other embodiments, germanium-68 is substituted for an amount of silicon in the structure (e.g., up to about 30% of the silicon atoms). The molar ratio of germanium-68 to silicon in the starting mixture may be selected to achieve the desired activity and, as in some embodiments, may be at least about 1:1000 or, as in other embodiments, at least about 1:1000, at least about 1:100, at least about 1:50, at least about 1:20, at least about 1:10 or at least about 1:5.

Matrix material such as zeolites may be prepared by forming an admixture or gel of the base material and maintaining crystallization conditions until crystals form. As crystals begin to form, the tetrahedra form a three dimensional network by sharing oxygen atoms.

In some embodiments, an aqueous mixture of germanium-68 oxide ($^{68}GeO_2$) and one or more other oxides is prepared (e.g., silica, alumina and/or stable germania) and heated to form crystals. As an alternative to use of germania, a germanium halide such as germanium chloride ($^{68}GeCl_4$) may be added to the zeolite formation mixture. Suitable crystallization conditions may include heating under hydrothermal conditions. For example, the crystallization starting mixture or gel may be heated to at least about 100° C. or even to at least about 150° C. (e.g., from about 100° C. to about 200° C.). Upon heating, the starting mixture crystallizes and forms tetrahedra of the first central atom and germanium-68 tetrahedra in the crystallized structure.

Suitable methods for forming the matrix material (e.g., zeolite material) may involve use of various structure directing agents (SDAs) including organic or inorganic agents which assist in formation of the three-dimensional structures. Exemplary SDAs include inorganic cations, phosphazenes, quaternary ammonium compounds (e.g., halides and hydroxides), imidazolium compounds and cyclic and linear ethers. Seed-assisted methods may also be used to promote crystallization and/or structure formation. Seed-assisted methods may involve use of seed crystals of the desired structure which act as crystal growth surfaces for formation of the matrix material.

After crystallization, the zeolite crystals may be separated from the liquid portion of the gel by filtration or evaporation. The crystals may be washed (e.g., with water) to remove residual liquids and fine crystals. In some embodiments, the crystalline material is calcined.

In some embodiments, the starting mixture is a gel having formula (1)

$$xGeO_2 ySiO_2 \qquad (1),$$

with (x, y) being (0.8, 0.2), (0.4, 0.6) or (0.165, 0.835).

In some embodiments, the second central atom is silicon. Alternatively or in addition, the starting mixture may comprise a source of third central atoms (such as in zeolite structures which also comprise germanium-68). If the second central atom is silicon, the third may be selected from the group consisting of aluminum, zirconium and stable germanium.

In some embodiments, the molar ratio of stable germanium to germanium-68 in the staring material and the resulting crystallized material is controlled to adjust the activity of the calibration device. Generally, lowering the ratio of stable germanium to germanium-68 results in more active calibration devices and vice versa.

Figure 2:
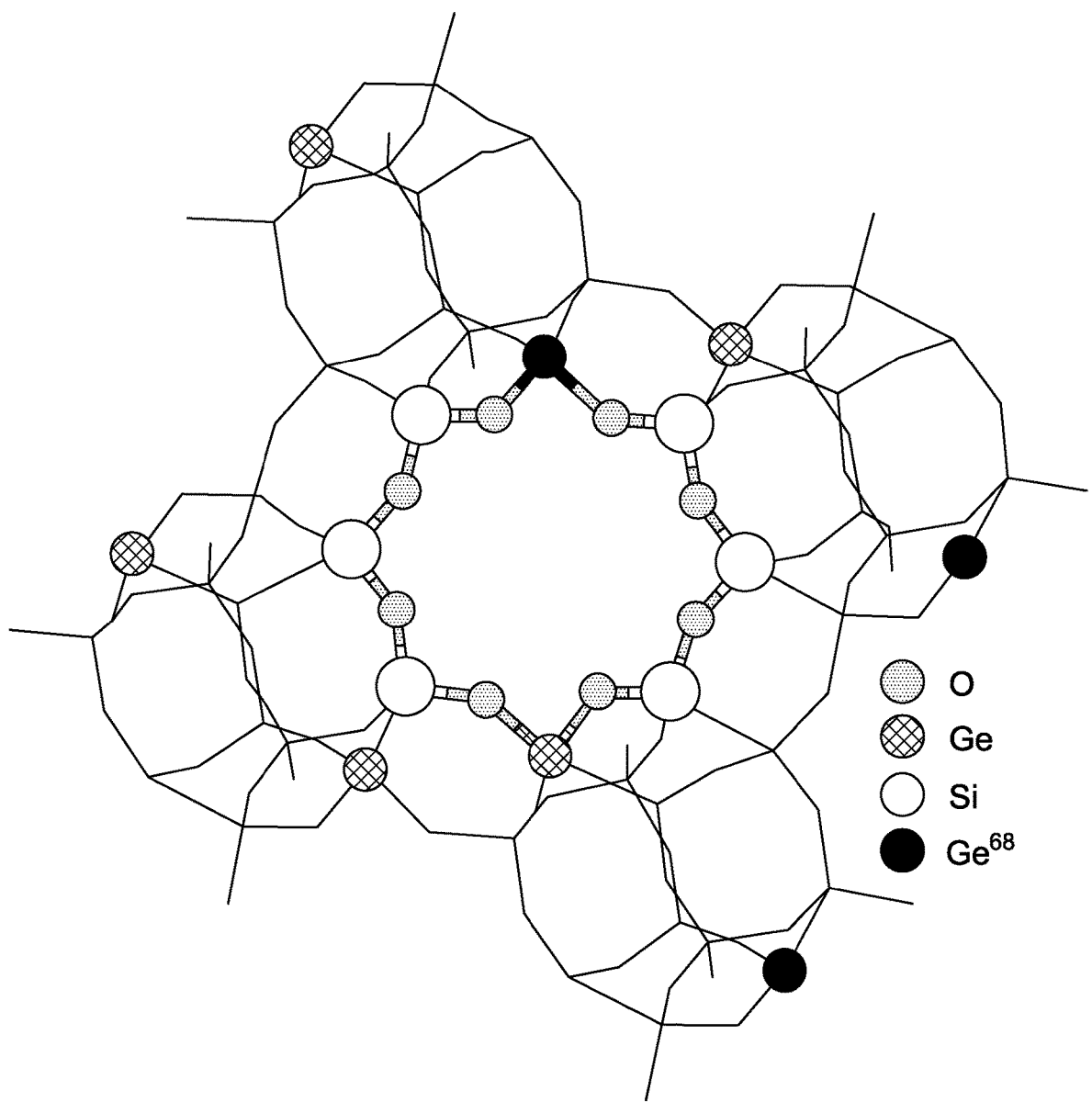
FIG. 2 is a schematic of a chabazite zeolite structure having a main cavity in an 8T ring with germanium-68 isomorphously being substituted for stable germanium.

The resulting germanium-68 zeolite frameworks may have any suitable shape such as, for example, cubic structures as described in O'Keeffe et al., "Germanate Zeolites: Contrasting the Behavior of Germanate and Silicate Structures being from Cubic $T_8O_{20}$ Units (T=Ge or Si)", Chem. Eur. J. 1999, 5 (10) which is incorporated herein by reference for all relevant and consistent purposes. Other frameworks such as Zeolite A (Linde Type A) or chains of 6-membered rings such as Zeolite Y (Linde Type Y) or chabazite, mordenite or ferrierite may also be prepared (see Davis et al., "Zeolite and Molecular Sieve Synthesis", Chem. Mater. 1992, 4(4) pp. 756-768 and Davis, "Zeolites from a Materials Chemistry Perspective," Chem. Mater., 2014, 26(1), pp. 239-245, both of which are incorporated herein by reference for all relevant and consistent purposes). An exemplary chabazite zeolite structure in which germanium-68 is isomorphously substituted for a portion of non-active germanium atoms is shown in FIG. 2.

Figure 3:
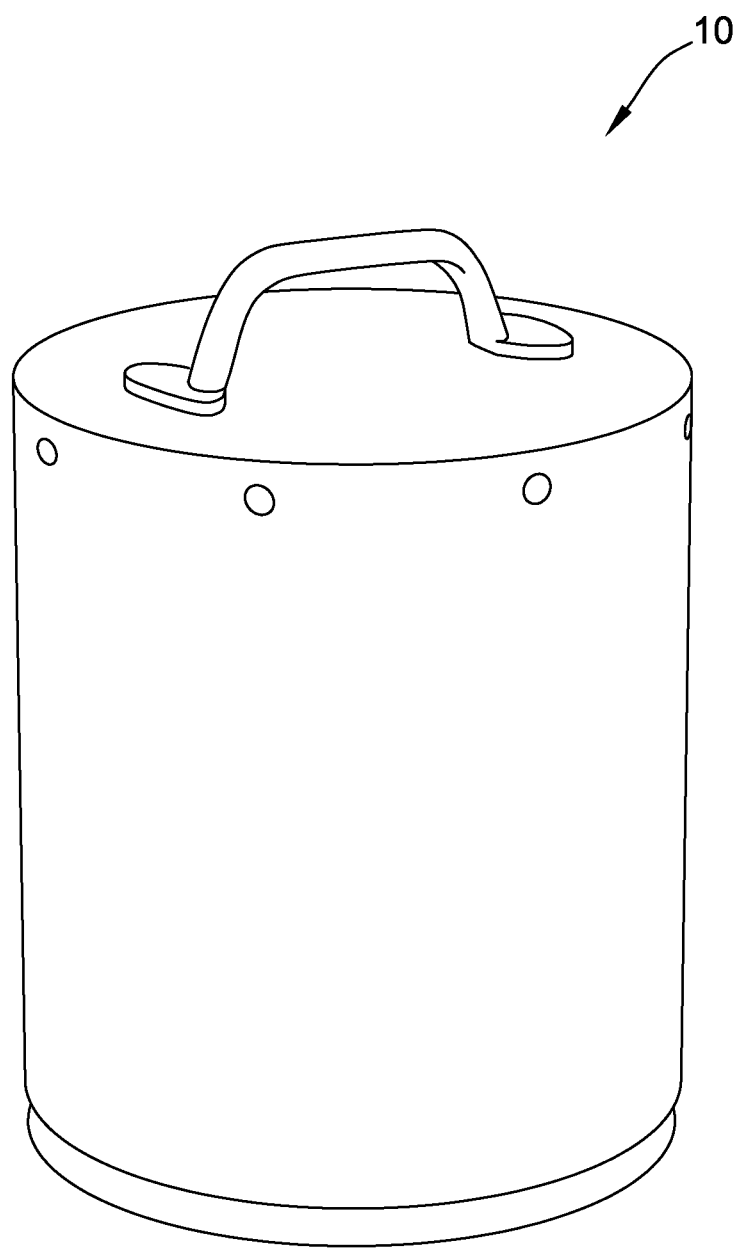
FIG. 3 is a perspective view of a cylindrical calibration device.

After formation, the germanium-68 substituted matrix material is formed into a suitable shape for calibration of radiation detectors. The matrix material may be used as powder in the calibration source with the powder being contained within a housing of suitable shape. The matrix material may be mixed with various resins, binders, fillers, ceramics (e.g., alumina) and other excipients and formed into various shapes (e.g., pellets, rods, blocks and the like). In some embodiments and as shown in FIG. 3, the matrix material is formed into a phantom such as a cylindrical phantom 10 that may be used for calibration of a PET scanner. In other embodiments, the material is formed into a rod such as for line calibration sources.

The calibration device may include a housing that holds the germanium-68 substituted matrix material. The device may include a radiation shield (e.g., lead shield) that may be removed during calibration of the radiation detector. In some embodiments, the germanium-68 substituted matrix material is housed within a vial.

The germanium-68 calibration device emits a known amount of radiation. This allows the device to act as a standard to which the radiation measured by the radiation detector is compared. Suitable radiation detectors which may be calibrated include PET scanners and cameras and gamma cameras and spectrometers.

To calibrate the detector, the calibration device is positioned in the detection field of the detector. The radiation detector is operated to detect radiation emitted by the calibration device. The detected radiation may be compared to the amount of radiation that was expected to be emitted by the calibration device. A difference (or lack of difference if properly calibrated) may be used to normalize data generated by the radiation detector. For example, data generated by two or more detectors (e.g., different scanners or cameras at different medical sites) may be normalized to reduce measurement variations between scanners. In some embodiments, any measured difference between detected radiation and the expected radiation (i.e., the standard) is used to re-calibrate the detector through one or more adjustment protocols.

Compared to conventional germanium-68 calibration devices, the calibration devices of embodiments of the present disclosure have several advantages. By isomorphously including germanium-68 into the framework and crystal structure of the material, germanium-68 is not readily leached from the material. The matrix material is a solid-state inorganic material with high chemical, radiation and mechanical resistance. The activity of the calibration device may be controlled by adjusting the ratio of germanium-68 to non-active germanium in the starting material used to prepare the crystalline matrix material. By isomorphously binding germanium-68, the germanium-68 crystalline matrix material may be easily handled during source fabrication and source material disposal.

As used herein, the terms "about," "substantially," "essentially" and "approximately" when used in conjunction with ranges of dimensions, concentrations, temperatures or other physical or chemical properties or characteristics is meant to cover variations that may exist in the upper and/or lower limits of the ranges of the properties or characteristics, including, for example, variations resulting from rounding, measurement methodology or other statistical variation.

When introducing elements of the present disclosure or the embodiment(s) thereof, the articles "a", "an", "the" and "said" are intended to mean that there are one or more of the elements. The terms "comprising," "including," "containing" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above constructions and methods without departing from the scope of the disclosure, it is intended that all matter contained in the above description and shown in the accompanying drawing [s] shall be interpreted as illustrative and not in a limiting sense.

What is claimed is:

1. A solid-state germanium-68 source material comprising:
   a matrix material having a three-dimensional polyhedral crystal structure, the matrix material comprising:
   a first tetrahedra comprising a central atom, T, and oxygen, the central atom being selected from the group consisting of silicon, aluminum, zirconium and stable germanium, the first tetrahedra having a formula $TO_4$; and
   a second tetrahedra, the second tetrahedra being a germanium-68 tetrahedra comprising germanium-68 and oxygen and having a formula $^{68}GeO_4$, the first tetrahedra and germanium-68 tetrahedra being part of a three-dimensional polyhedral crystal structure.

2. The solid-state germanium-68 source material as set forth in claim 1 wherein the first tetrahedra is a silicon tetrahedra having a formula $SiO_4$, germanium-68 being isomorphously substituted for silicon as the central atom of a plurality of tetrahedra in the matrix material.

3. The solid-state germanium-68 source material as set forth in claim 1 wherein the matrix material further comprises a third tetrahedra, the third tetrahedra comprising a central atom selected from the group consisting of silicon, aluminum, zirconium and stable germanium.

4. The solid-state germanium-68 source material as set forth in claim 3 wherein the third tetrahedra is an aluminum tetrahedra, the aluminum tetrahedra comprising aluminum and oxygen and having a formula $AlO_4$.

5. The solid-state germanium-68 source material as set forth in claim 3 wherein the third tetrahedra is a stable germanium tetrahedra, the stable germanium tetrahedra comprising stable germanium and oxygen and having a formula $GeO_4$.

6. The solid-state germanium-68 source material as set forth in claim 5 wherein the stable germanium is isomorphously substituted for silicon as the central atom of a plurality of tetrahedra in the matrix material.

7. A method for calibrating a radiation detector, the method comprising:
positioning a calibration device comprising the solid-state germanium-68 source material as set forth in claim 1 in a detection field of the detector;
operating the radiation detector to detect radiation emitted by the calibration device; and
comparing the detected radiation to an expected amount of radiation emitted by the calibration device.

8. A method for producing a germanium-68 source material, the source material comprising a matrix material with germanium-68 isomorphously substituted therein, the method comprising:
forming a crystallization starting mixture, the starting mixture having a source of a first central atom and a source of a second central atom, the first central atom being germanium-68 and the second central atom being selected from the group consisting of silicon, aluminum, zirconium and stable germanium; and
heating the starting mixture to cause the material to crystallize and form germanium-68 tetrahedra and tetrahedra of the second central atom in a crystallized structure.

9. The method a set forth in claim 8 wherein the second central atom is silicon.

10. The method as set forth in claim 9 wherein the crystallization starting mixture further comprises a third central atom selected from the group consisting of aluminum, zirconium and stable germanium, the crystallized structure comprising tetrahedra of the third central atom.

11. The method as set forth in claim 8 wherein the starting mixture is heated to at least about 100° C. and the matrix material is crystallized under hydrothermal conditions.

12. The method as set forth in claim 8 wherein the first central atom is silicon, the molar ratio of germanium-68 to silicon in the starting mixture being at least about 1:1000.

13. The method as set forth in claim 8 wherein a germanium-68 halide is added to the starting mixture as a source of germanium-68.

14. The method as set forth in claim 8 wherein a $^{68}GeO_2$ is added to the starting mixture as a source of germanium-68.

15. The method as set forth in claim 8 wherein the second central atom is silicon, silica being added to the starting mixture as a source of silicon.

16. The method as set forth in claim 8 wherein the starting mixture is a gel.

17. The method as set forth in claim 16 wherein the gel comprises silica and stable germania according to the formula $xGeO_2 ySiO_2$.

18. The method as set forth in claim 17 wherein y is equal to (1−x) and x is 0.8, 0.4 or 0.165.

19. The method as set forth in claim 8 wherein the matrix material has a three-dimensional polyhedral crystal structure.

20. A method for producing a calibration device that comprises germanium-68, the method comprising:
producing a germanium-68 source material by the method as set forth in claim 8; and
forming the germanium-68 source material into a calibration device.

* * * * *